United States Patent
Watanabe et al.

(10) Patent No.: US 7,015,370 B2
(45) Date of Patent: Mar. 21, 2006

(54) DISPOSABLE WEARING ARTICLE FOR FLUID DISTRIBUTION HAVING FILLED VOID, DENSITY GRADIENT AND SPACER MEMBERS

(75) Inventors: Maki Watanabe, Kagawa-ken (JP); Miou Suzuki, Kagawa-ken (JP); Masashi Nakashita, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 224 days.

(21) Appl. No.: 10/634,081

(22) Filed: Aug. 4, 2003

(65) Prior Publication Data
US 2004/0030313 A1    Feb. 12, 2004

(30) Foreign Application Priority Data
Aug. 9, 2002    (JP) ............................. 2002-233004

(51) Int. Cl.
*A61F 13/537* (2006.01)
*A61F 13/15* (2006.01)

(52) U.S. Cl. ............... 604/378; 604/379; 604/385.101; 604/367

(58) Field of Classification Search ........ 604/378–381, 604/367, 385.101, 385.01, 358
See application file for complete search history.

(56) References Cited

U.S. PATENT DOCUMENTS

| 3,768,480 | A |  | 10/1973 | Mesek et al. |
| 4,027,672 | A | * | 6/1977 | Karami ........................ 604/380 |
| 5,411,497 | A | * | 5/1995 | Tanzer et al. ................ 604/368 |
| 5,454,800 | A |  | 10/1995 | Hirt et al. |
| 5,500,270 | A | * | 3/1996 | Langdon et al. ............ 428/119 |
| 5,505,720 | A |  | 4/1996 | Walters et al. |
| 5,578,024 | A | * | 11/1996 | Mizutani et al. ............ 604/380 |
| 5,591,148 | A |  | 1/1997 | McFall et al. |
| 5,683,374 | A | * | 11/1997 | Yamamoto et al. ..... 604/385.29 |
| 5,785,697 | A | * | 7/1998 | Trombetta et al. .......... 604/378 |
| 6,177,605 | B1 |  | 1/2001 | Trombetta et al. |
| 2002/0026169 | A1 | * | 2/2002 | Takai et al. ................. 604/378 |
| 2002/0029024 | A1 | * | 3/2002 | Furuya et al. .............. 604/378 |
| 2002/0040211 | A1 | * | 4/2002 | Drevik ........................ 604/378 |
| 2002/0040212 | A1 | * | 4/2002 | Drevik ........................ 604/380 |
| 2002/0052587 | A1 |  | 5/2002 | Magnusson et al. |

FOREIGN PATENT DOCUMENTS

| EP | 0 804 915 A1 |  | 11/1997 |
| WO | WO 9301780 A1 | * | 2/1993 |
| WO | WO 03/061541 A2 |  | 7/2003 |

* cited by examiner

*Primary Examiner*—Tatyana Zalukaeva
*Assistant Examiner*—L C Hill
(74) *Attorney, Agent, or Firm*—Butzel Long

(57) ABSTRACT

A wearing article absorption of body fluids has an inner sheet, an outer sheet and a body fluid absorbent first panel underlying the inner sheet. The inner sheet and the first panel are formed in central regions thereof with a void to be filled with a hydrophobic second panel which is elastically compressible and liquid-pervious. A plurality of narrow strips, each comprising water-absorbent fibers compressed to a high density, and a hydrophobic and liquid-pervious spacer member underlying the narrow strips are interposed between the second panel and the outer sheet.

5 Claims, 4 Drawing Sheets

«DISPOSABLE WEARING ARTICLE FOR FLUID DISTRIBUTION HAVING FILLED VOID, DENSITY GRADIENT AND SPACER MEMBERS

BACKGROUND OF THE INVENTION

The present invention relates to a disposable wearing article for rapid absorption and diffusion of body fluids such as urine.

The disposable wearing article for absorption of body fluids is well known, which comprises a liquid-pervious inner sheet facing the wearer's body, a liquid-impervious outer sheet facing the wearer's clothes and an absorbent panel including water-absorbent fibers and interposed between these two sheets. Such a wearing article is usually used as a disposable diaper, disposable training pants or an absorbing pad for the incontinence of urine. For example, when the wearing article is used as a disposable diaper, the wearing article is configured in pull-on type to be put on the wearer's body or the wearing article is configured to be attached to the holder member such as a reusable or disposable diaper cover.

When the conventional wearing article as has been described above is used as the disposable diaper, the absorbent panel extends over a crotch region and further extends into front and rear waist regions. To ensure that the amount of urine discharged in the crotch region can spread all over the absorbent panel, the panel is often formed with the body fluid diffusible zone extending over the crotch region and extending further into the front and rear waist regions and comprising water-absorbent fibers compressed to a high density. In the diffusible zone, the water-absorbent fibers such as fluff pulp constituting the panel are assembled at a high density, the amount of urine may spread through this diffusible zone to the portions of the panel lying in the front and rear waist regions. However, in the crotch region, water-absorbing capacity is readily saturated even in the diffusible zone and the diffusible zone containing a large amount of urine may directly come in contact with the wearer's body and create an uncomfortable feeling of wetness against the wearer.

SUMMARY OF THE INVENTION

It is an object of the present invention to provide a disposable wearing article for absorption of body fluids improved so that the body fluids having been absorbed by the disposable wearing article can spread to desired regions of this wearing article and the body fluid diffusible zone never create an uncomfortable feeling of wetness against a wearer.

According to the present invention, there is provided a disposable wearing article for absorption of body fluids having longitudinal direction, a transverse direction and a thickness direction and comprising an inner sheet lying in the top in the thickness direction so as to face the wearer's body, an outer sheet lying in the bottom in said thickness direction and a body fluid absorbent first panel interposed between the inner and outer sheets and containing water-absorbent fibers.

The improvement according to the present invention further comprises the inner sheet formed by a liquid-pervious sheet or a liquid-impervious sheet, and the outer sheet is formed by a liquid-impervious sheet, and the inner sheet and the first panel underlying the inner sheet lacking a part of a substantially central portion in the longitudinal direction as well as in the transverse direction as cut off so as to define a void, the void being filled with a second panel which is liquid-pervious hydrophobic and have compressive elasticity in the thickness direction, a plurality of narrow strips extending parallel to one another in one of the longitudinal and transverse directions beyond the second panel and spaced apart from one another so as to come in contact with a lower surface of the first panel, the narrow strips containing therein water-absorbent fibers compressed to a density higher than that of the water-absorbent fibers in the first panel and a hydrophobic liquid-pervious spacer member lying aside from the narrow strips toward the outer sheet and extending beyond the second panel in both the longitudinal direction and the transverse direction to space parts of the first panel and parts of the narrow strips apart from the outer sheet toward the inner sheet.

The present invention includes the following embodiments.

The first panel comprises 100 to 10 wt % of water-absorbent fiber and 0 to 90 wt % of super-absorbent polymer and the water-absorbent fiber in the first panel has a density of 0.04 to 0.10 g/cm$^3$.

Each of the narrow strips comprises 100 to 20 wt % of water-absorbent fiber, 0 to 80 wt % of super-absorbent polymer and 0 to 20 wt % of thermoplastic synthetic fiber and the water-absorbent fiber of the narrow strip has a density of 0.10 to 0.40 g/cm$^3$ at least 0.03 g/cm$^3$ higher than that of the water-absorbent fiber in the first panel.

The second panel comprises a first layer lying aside toward the inner sheet and a second layer lying aside toward the outer sheet both as viewed in the thickness direction, the first layer being formed by a laminate of thermoplastic synthetic resin film and thermoplastic synthetic fiber placed on the inner side of the film and the second layer being formed by opened-cell polyurethane foam, the laminate forming a plurality of narrow strips extending adjacent to one another in one of the longitudinal and transverse directions, and each of the narrow strips being formed on its upper surface with alternate crests and troughs repeated in a longitudinal direction of the narrow strip so that the crests in one of the narrow strips lie adjacent to the troughs in the other narrow strip adjacent to the one of the narrow strips and the thermoplastic synthetic fibers are exposed on side surfaces of the crests.

The second panel comprises a porous liquid-pervious thermoplastic synthetic resin sheet.

DETAILED DESCRIPTION OF THE PREFERRED EMBODIMENTS

Details of the wearing article for absorption of body fluids according to the present invention will be more fully understood from the description given hereunder with reference to the accompanying drawings.

Figure 1:
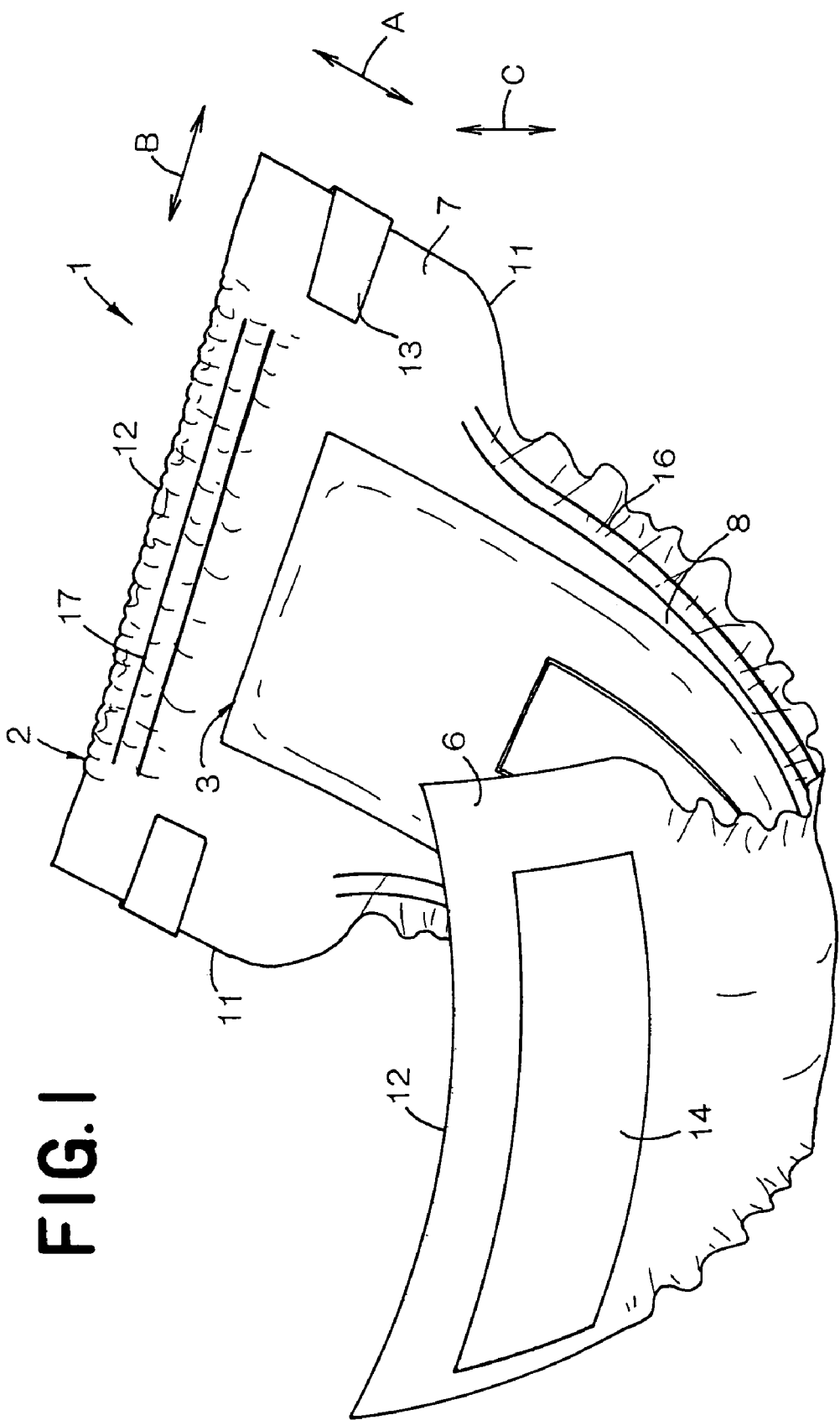
FIG. 1 is a perspective view showing a disposable diaper.

FIG. 1 is a perspective view of a disposable diaper 1. The diaper 1 generally comprises a cover member 2 presenting an hourglass-shape as viewed in its developed state and a body fluid absorbent member 3, the most important feature of the present invention, presenting a rectangular shape also as viewed in its developed state.

The cover member 2 is formed, for example, by a laminated sheet consisting of thermoplastic synthetic resin film and nonwoven fabric. The film may define inner or outer surface of this cover member 2. The cover member 2 has a longitudinal direction A, a transverse direction B and a thickness direction C and defines, in the longitudinal direction A, a front waist region 6, a rear waist region 7 and a crotch region 8 extending between these two waist regions 6, 7. A peripheral edge of the cover member 2 comprises a pair of transversely opposite side edges 11 extending in the longitudinal direction A and a pair of longitudinally opposite ends 12 extending in the transverse direction B. In the rear waist region 7, a pair of tape fasteners 13 are attached to the vicinity of the side edges 11, respectively. When the diaper 1 is put on the wearer's body, these tape fasteners 13 are adapted to be laterally unfolded and then to be releasably anchored on a target zone 14 formed on the outer surface of the front waist region 6. A plurality of elastic elements 16, 17 are attached in a stretched state to the inner surface of the cover member 2 along the side edges 11 and the ends 12, respectively.

The body fluid absorbent member 3 is attached to the inner surface of the cover member 2 so as to extend over the crotch region 8 and further extend into the front waist region 6 and the rear waist region 7. The absorbent member 3 may be secured to the cover member 2 by means of adhesion or heat-sealing. It is possible that the absorbent member 3 is releasably attached to the cover member 2 by means of a mechanical fastener (See FIG. 4) commonly known in the trade name of Magic Tape or Velcro tape or a self-adhesive agent. The absorbent member 3 attached to the cover member 2 in this manner preferably lies inside the boundary line defined by the elastic members 16, 17 extending along the side edges 11 and the ends 12 of the cover member 2, respectively, as will be seen in FIG. 1.

Figure 2:
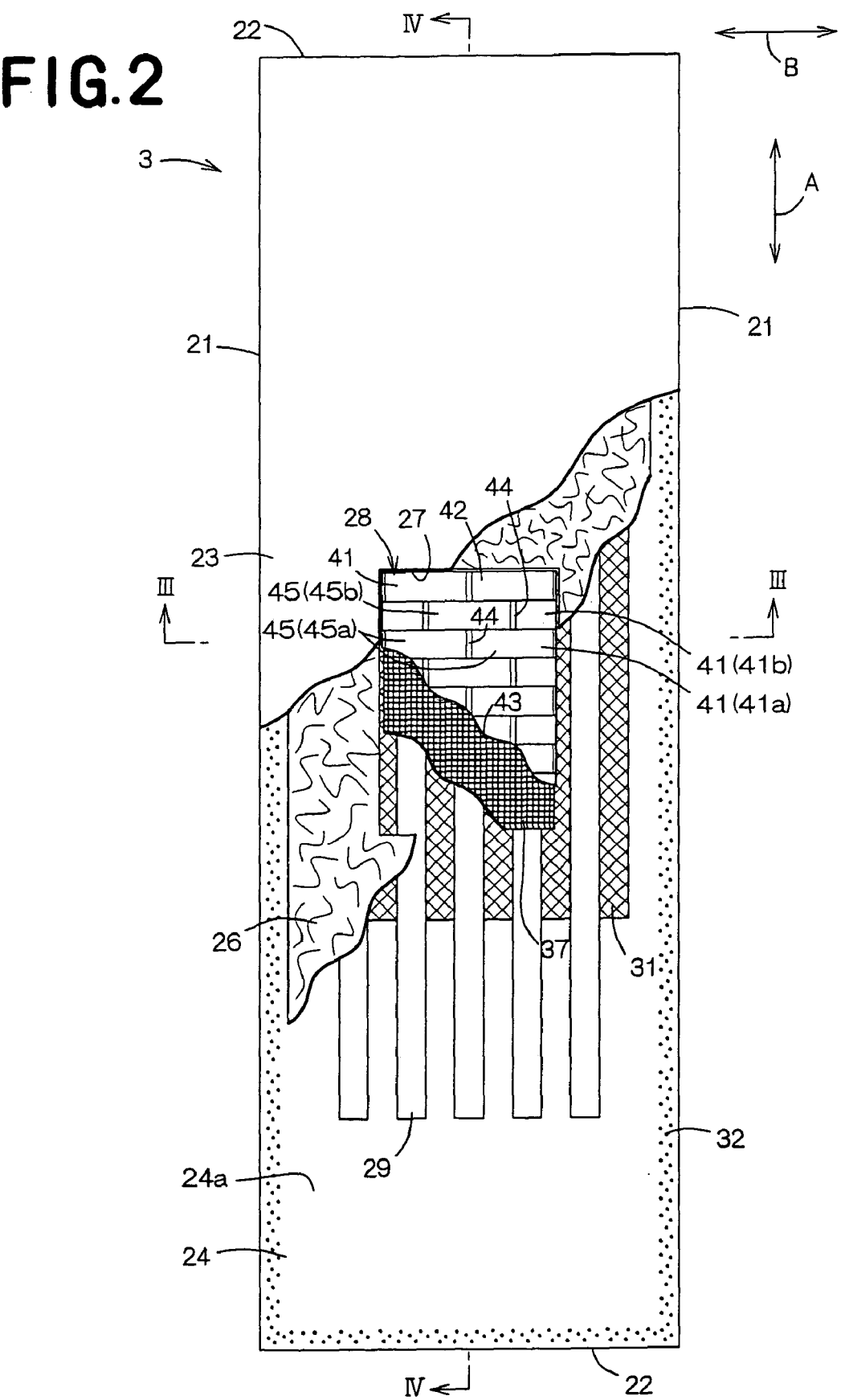
FIG. 2 is a partially cutaway plan view showing an absorbent member.
Figure 3:
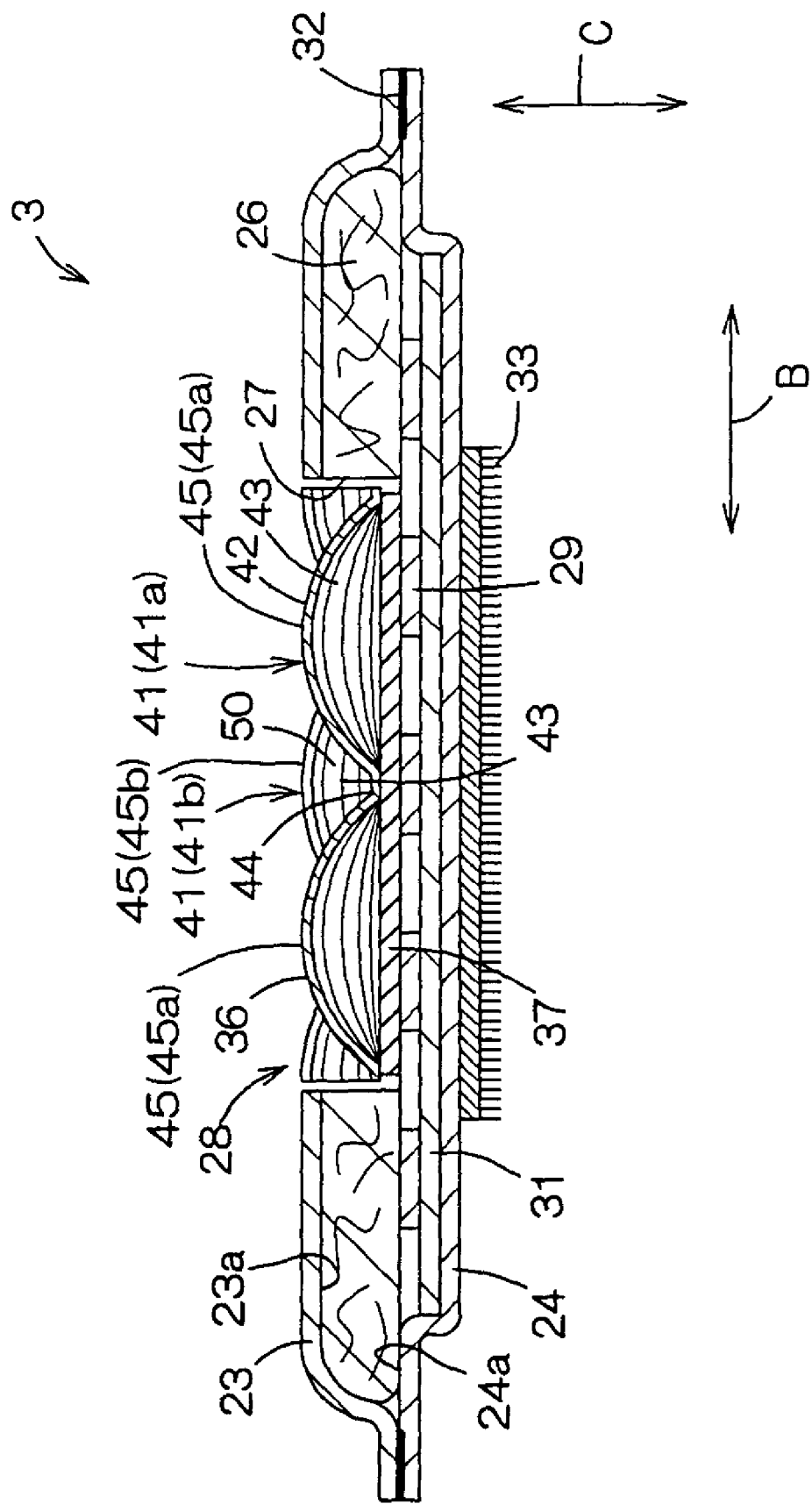
FIG. 3 is a scale-enlarged sectional view taken along a line III—III in FIG. 2.
Figure 4:
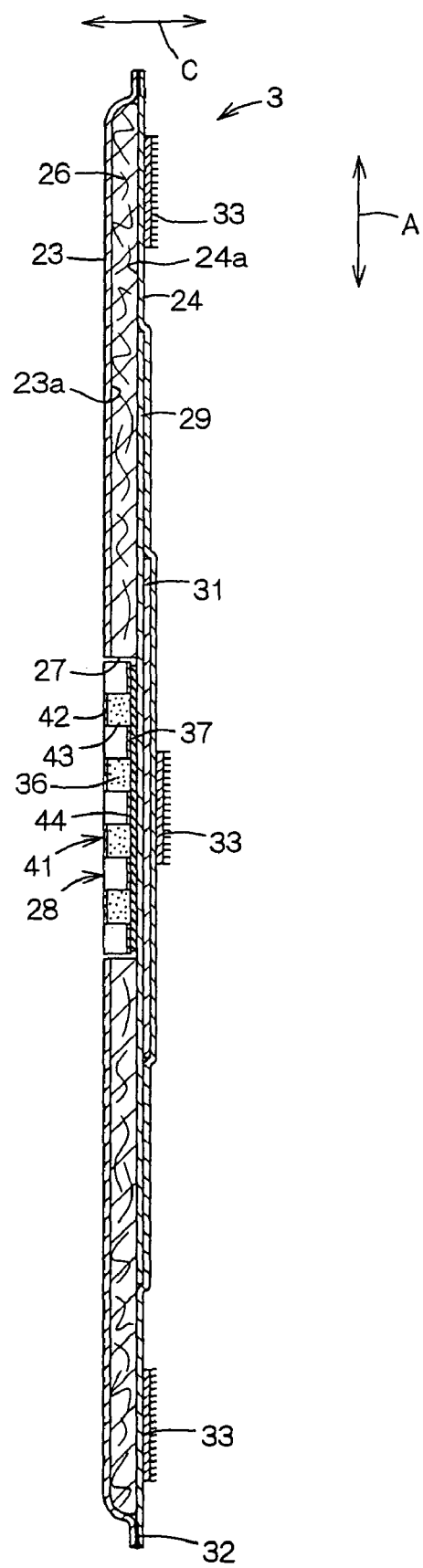
FIG. 4 is a sectional view taken along a line IV—IV in FIG. 2.

FIG. 2 is a partially cutaway plan view showing the absorbent member 3, FIG. 3 is a scale-enlarged sectional view thereof taken along a line III—III in FIG. 2 and FIG. 4 is a sectional view thereof taken along a line IV—IV in FIG. 2. Similarly to the cover member 2, the absorbent member 3 has the longitudinal direction A, the transverse direction B and the thickness direction C. A peripheral edge of the absorbent member 3 is defined by a pair of transversely opposite side edges 21 extending in the longitudinal direction A and a pair of longitudinally opposite ends 22 extending in the transverse direction B. In a flattened state, the absorbent member 3 present a rectangle contoured by this peripheral edge, which is relatively long in the longitudinal direction A. While either the size nor the shape is particularly specified for the absorbent member 3, in one preferred embodiment illustrated in FIGS. 2, 3 and 4, the respective side edges 21 have a dimension in a range of 200 to 450 mm and the respective ends 22 have a dimension in a range of 60 to 130 mm. The absorbent member 3 includes an inner sheet 23 facing the wearer's body, an outer sheet 24 facing the cover member 2 and a first panel 26 for absorption of body fluid. The first panel 26 is kept in close contact with a lower surface 23a of the inner sheet 23. The inner sheet 23 lies in the top of the absorbent member 3 in the thickness direction C, the outer sheet 24 lies in the bottom of the absorbent member 3 in the thickness direction C as viewed in FIG. 3. The inner sheet 23 and the first panel 26 lack a part for the substantially central portion in the longitudinal direction A as well as in the transverse direction B as cut off by rectangular shape so as to define a void 27. In the case of the illustrated embodiment, this void 27 is dimensioned to be in a range of 40 to 110 mm in the longitudinal direction A and to be in a range of 30 to 80 mm in the transverse direction B. This void 27 is filled with a body fluid pervious second panel 28 having a body fluid permeability. The first panel 26 and the second panel 28 are provided on lower side thereof with a plurality of narrow strips 29 for absorption and diffusion of body fluid. The narrow strips 29 are provided on lower side thereof with a spacer member 31 having a body fluid permeability. In the illustrated embodiment, the void 27 can be appropriately shifted in the longitudinal direction A if desired.

The inner sheet 23 may be formed by a liquid-pervious sheet or a liquid-impervious sheet. As a liquid-pervious sheet, a nonwoven fabric or apertured thermoplastic synthetic resin film may be used, as a liquid-impervious sheet, a thermoplastic synthetic resin film or a composite sheet consisting of the thermoplastic resin film and nonwoven fabric laminated thereon so that the nonwoven fabric faces the wearer's body may be used.

The outer sheet 24 is of liquid-impervious nature and, as stock material for this sheet, thermoplastic synthetic resin film or a composite sheet consisting of such film and nonwoven fabric laminated on the film so as to face the cover member 2 may be used. The inner and outer sheets 23, 24 are overlaid and joined together outward beyond a peripheral edge of the first panel 26 by means of adhesive agent 32 or using heat-sealing technique. The outer sheet 24 is provided on its surface facing the cover member 2 with fastening zones 33. The outer sheet 24 can be attached to the cover member 2 releasably or not releasably by means of the fastening zones 33. In case that the fastening zones 33 are releasably attached to the outer sheet 24, for example, a hook member and a loop member constituting so-called mechanical fastener commonly known in the trade name of Magic Tape may be used. The outer sheet 24 may be provided with a hook member (See FIGS. 3 and 4) or a loop member, and the cover member 2 may be provided with a loop member or a hook member. It is also possible to form the fastening zone 33 by locally coating the outer sheet 24 with suitable adhesive agent.

The first panel 26 for absorption and containment of body fluids may comprise 100 to 10 wt % of water-absorbent fiber such as fluff pulp, 0 to 90 wt % of super-absorbent polymer in the form of particle or fiber and additionally 0 to 20 wt % of thermoplastic synthetic fiber. The water-absorbent fiber preferably has a basis weight of 250 to 650 g/m$^2$ and a density of 0.04 to 0.10 g/cm$^3$.

The second panel 28 defines a hydrophobic layer allowing body fluids to permeate the second panel 28 in the direction from the inner sheet 23 toward the outer sheet 24. The second panel 28 comprises, for example, an assembly of thermoplastic synthetic fibers, a laminate of thermoplastic synthetic fibers and thermoplastic synthetic resin films, a porous and liquid-pervious thermoplastic synthetic resin sheet such as a thermoplastic synthetic resin foam sheet, or a laminate of such sheets and thermoplastic synthetic fibers. The second panel 28 is an elastic body which is 2 to 10 mm thick after applied with a load of 3.5 g/cm$^2$ for 15 seconds and restores 50% or higher of its initial thickness within 60 seconds after the load has been removed. In the case of the illustrated embodiment, the second panel 28 comprises a first layer 36 placed aside toward the inner sheet 23 and a second layer 37 placed aside toward the outer sheet 24. The first layer 36 comprises an assembly of thermoplastic synthetic fibers, or a laminate consisting of thermoplastic synthetic fibers and thermoplastic synthetic resin films, contributing to make the surface of the second panel 28 flexible. A stock material for the assembly of thermoplastic synthetic fibers may be selected from a nonwoven fabric of short or continuous fibers and a fibrillated tow of continuous fibers, in any case, having a fineness of 0.1 to 32 dtx and a basis weight preferably of 50 to 500 g/m². The thermoplastic synthetic resin film preferably has a thickness of 5 to 30 µm and it is also possible to use a liquid-pervious apertured film for the same purpose. In the case of the illustrated embodiment, the first layer 36 comprises a plurality of narrow strips 41 adjacent to one another and extending in the transverse direction, each of the narrow strips 41 comprises a film 42 and an assembly of a plurality of continuous fibers 43 extending in the transverse direction B under the film 42. This assembly of continuous fibers 43 is obtained by fibrillating a tow, a bundle of the fibers 43. In depressed zones 44, the assembly of the fibers 43 and the film 42 are welded together by heating under a pressure and therefore the assembly of the fibers 43 is relatively thin. In each of the narrow strips 41, a crest 45 is defined between each pair of the depressed zones 44, 44 adjacent to each other, so crests and troughs defined by the crests 45 and the depressed zones 44 alternately appear in the longitudinal direction of this narrow strip 41. Referring to FIG. 3, a side surface 50 of the crest 45b of the narrow strip 41b is seen beyond the depressed zone 44 defined between the pair of the crests 45a, 45a adjacent to each other in the narrow strip 41a which is adjacent to the narrow strip 41b in the longitudinal direction A. The continuous fibers 43 expose on the side surface 50. The second layer 37 of the second panel 28 has a density of 0.02 to 0.10 g/cm³ and comprises a hydrophobic thermoplastic synthetic resin sheet which is porous, therefore, liquid-pervious and elastically compressible in the thickness direction C. It is possible to use an opened-cell urethane foam for the sheet. While the first layer 36 and the second layer 37 constituting the second panel 28 may be merely placed upon each other, it is also possible to join together intermittently using a suitable adhesive agent or a heat-sealing technique. It is also possible to arrange the narrow strips 41 so as to extend in the longitudinal direction A instead of arranging them so as to extend in the transverse direction B as in the illustrated.

Each of the narrow strips 29 contains 100 to 20 wt % of water-absorbent fiber such as fluff pulp or rayon. The water-absorbent fiber preferably has a density of 0.10 to 0.40 g/cm³ which is at least 0.03 g/cm³ higher than the density of the water-absorbent fiber in the first panel 26. Preferably, the narrow strip 29 has a thickness of 0.5 to 7 mm after applied with a load of 3.5 g/cm² for 15 seconds, a width of 5 to 30 mm and a length of 60 to 180 mm. Referring to FIGS. 2 and 4, the narrow strips 29 extend across the second panel 28 in the longitudinal direction A and put in contact with the lower surface of the first panel 26. In the transverse direction B, each pair of the narrow strips 29 adjacent to each other are spaced apart from each other by 3 to 20 mm. Preferably, each of the narrow strips 29 presents a rectangular cross-section and may be joined to the first and second panels 26, 28. It is also possible to arrange the narrow strips 29 so as to extend in the transverse direction B.

The spacer member 31 is formed by material such as an apertured film or net made of hydrophobic thermoplastic synthetic resin, a nonwoven fabric made of thermoplastic synthetic fiber having a fineness of 5 to 32 dtx, or a pervious sheet made of opened-cell urethane foam. Preferably, the spacer member 31 has a thickness in order of 0.3 to 2 mm. In the case of the spacer member 31 formed by an aperture film, it is preferable that the film has a plurality of apertures each having a diameter of 0.3 to 3 mm and a liquid passage having a height of 0.3 to 2 mm extends toward the outer sheet 24 from a peripheral edge of each aperture. When a net or a nonwoven fabric is used for the spacer member 31, a plurality of layers thereof are preferably laminated one another in a thickness of 0.3 to 2 mm. The spacer member 31 is larger than the second panel 28, peripheral edges of the spacer member 31 are located outside the peripheral edges of the second panel 28. Since the spacer member 31 is interposed between the first panel 26 and the narrow strips 29, the first panel 26 is spaced apart from the narrow strips 29 in the direction from the outer sheet 24 toward the inner sheet 23 by a dimension corresponding to the thickness of the spacer member 31 or by a dimension corresponding to the height of the liquid passage when the spacer member 31 is formed by the aperture film having the liquid passages. The spacer member 31 may be bonded to the narrow strips 29 and to the outer sheet 24.

The body fluid absorbent member 3 is used together with the cover member 2 so that the second panel 28 may be placed against the wearer's urethral or put on the wearer's body so that the second panel 28 may be located at the lowest position in the crotch region 8. Consequently, the amount of discharged urine permeates the second panel 28, and then, is caught in the narrow strips 29 or flows downward between each pair of the narrow strips 29 adjacent to each other. The amount of urine caught in the narrow strips 29 is diffused in the narrow strips 29 in the longitudinal direction A because of a relatively high density of the narrow strip 29, and then, absorbed and contained by the first panel 26 with which the narrow strips 29 come in contact. The amount of urine flowing downward between each pair of the narrow strips 29 adjacent to each other penetrates the spacer member 31 and reaches the outer sheet 24. This amount of urine flows over the inner surface 24a of the outer sheet 24 in the longitudinal direction A as well as in the transverse direction B beyond the spacer member 31 and then absorbed by the first panel 26. In this way, urine can be diffused in the body fluid absorbent member 3 to the vicinity of the transversely opposite side edges 21 and the longitudinally opposite ends 22 of the first panel 26 without staying in the central zone. With a consequence, it is not likely that the diaper 1 might create the uncomfortable feeling of wetness against the wearer and urine might leak beyond the crotch region 8. Because the amount of urine flows over the inner surface 24a of the outer sheet 24 between the spacer member 31 and the outer sheet 24, the amount of urine can easily spread in the front and rear waist regions 6, 7 without staying in the crotch region 8 when the wearer is in lying down posture.

If the inner sheet 23 of the body fluid absorbent member 3 is liquid-impervious, discharged urine flows over the inner sheet 23 toward the second panel 28 in the crotch region 8 and penetrates into the second panel 28, and then, is absorbed by the first panel 26. If the inner sheet 23 is liquid-pervious, discharged urine may be absorbed by the first panel 26 after penetration into the inner sheet 23. The second panel 28 is preferably dimensioned to have a width corresponding to ¼ to ¾ of the width of the first panel 26 and a length corresponding to 2/10 to 9/10 pf the length of the first panel 26. The second panel 28 is interposed between the outer sheet 24 and the wearer's body and thereby prevents the narrow strips 29 wetted with urine absorbed therein from coming in contact with the wearer's body and at the same time prevents the amount of urine staying between the outer sheet 24 and the spacer member 31 from coming in contact with the wearer's body. To heighten the preventive effects, the second panel 28 has a compressive elasticity in the thickness direction so that the second panel 28 is not permanently deformed even when a body weight of the wearer is exerted thereupon. The second layer 37 as shown in FIGS. is a preferable example of means adapted to provide the second panel 28 with the elasticity. If the first layer 36 covering this second layer 37 to give the second panel 28 softness and flexibility is formed by a laminate of liquid-impervious film and fiber, the amount of urine flowing into the depressed zones 44 defining the troughs of the narrow strip 41, for example, the narrow strip 41a, as shown in FIG. 3, flows downward beyond the second panel 28 through interstices of the continuous fibers 43 exposed on the side surface 50 of the crest 45b of the narrow strip 41b adjacent to the narrow strip 41a in the longitudinal direction A.

While the body fluid absorbent member 3 according to the invention has been illustrated and described as the article constituting the diaper 1 with the cover member 2, the body fluid absorbent member 3 may be the article to be put on the wearer's body without utilizing the cover member 2. In that case, the inner sheet 23 and the outer sheet 24 are contoured to have planar shapes different from those as illustrated or sheet members of appropriate shapes are attached to the body fluid absorbent member 3 in the vicinity of its transversely opposite side edges 21 so that the body fluid absorbent member 3 can function also as a cover member.

The disposable body fluid absorbent wearing article according to the present invention has advantageous effects that the body fluids can spread from the central region to the peripheral region of the first panel because the second panel located in the substantially central region thereof has a compressive elasticity and is liquid-pervious and hydrophobic and provided on its underside with the narrow strips adapted to diffuse body fluids and the spacer member adapted to space the second panel and the narrow strips apart from the outer sheet. Because the narrow strips are covered with the second panel, it is not likely that the wearer might experience an uncomfortable feeling of wetness.

What is claimed is:

1. A disposable wearing article for absorption of body fluids having a longitudinal direction, a transverse direction and a thickness direction said disposable wearing article comprising:
    an inner sheet lying in a top in said thickness direction so as to face a wearer's body;
    an outer sheet lying in a bottom in said thickness direction; and
    a body fluid absorbent first panel interposed between said inner and outer sheets and containing water-absorbent fibers,
    said inner sheet comprising a liquid-pervious sheet or a liquid-impervious sheet and said outer sheet comprising a liquid-impervious sheet; and
    said inner sheet and said first panel underlying said inner sheet lacking a part of a substantially central portion in said longitudinal direction as well as in said transverse direction as cut off so as to define a void, said void being filled with a second panel which is liquid-pervious and hydrophobic and has compressive elasticity in said thickness direction,
    said disposable wearing article further comprising:
        a plurality of narrow strips extending parallel to one another in one of said longitudinal and transverse directions beyond said second panel which narrow strips are spaced apart from one another so as to come in contact with a lower surface of said first panel, said narrow strips containing therein water-absorbent fibers compressed to a density higher than that of said water-absorbent fibers of said first panel; and
        a hydrophobic liquid-pervious spacer member lying aside from said narrow strips toward said outer sheet and extending beyond said second panel in bath said longitudinal direction and said transverse direction to space said first panel and parts of said narrow strips apart from said outer sheet toward said inner sheet.

2. The wearing article according to claim 1, wherein said first panel comprises 100 to 10 wt. % of the water-absorbent fibers and 0 to 90 wt % of a super-absorbent polymer and said water-absorbent fibers in said first panel have a density of 0.04 to 0.10 g/cm.sup.3.

3. The wearing article according to claim 1, wherein each of said plurality of narrow strips comprises 100 to 20 wt % of water-absotbent fibers, 0 to 80 wt % of super-absorbent polymer and 0 to 20 wt % of thermoplastic synthetic fibers and said water-absorbent fibers of said plurality of narrow strips has a density of 0.10 to 0.40 g/cm$^3$ at least 0.03 g/cm$^3$ higher than that of said water-absorbent fibers in said first panel.

4. The wearing article according to claim 1, wherein said second panel comprises a first layer lying aside toward said inner sheet and a second layer lying aside toward said outer sheet both as viewed in said thickness direction, said first layer being formed by a laminate of thermoplastic synthetic resin film and thermoplastic synthetic fibers placed on the inner side of said film and said second layer being formed by opened-cell polyurethane foam, said laminate forming a plurality of narrow strips extending adjacent to one another in one of said longitudinal and transverse directions, and each of said ulurality of narrow strips being formed on an upper surface with crests and troughs that alternate in a longitudinal direction of said narrow strips so that said crests in one of said narrow strips lie adjacent to said troughs in an adjacent narrow strip and said thermoplastic synthetic fibers are exposed on side surfaces of said crests, crests, said troughs being defined by and between the crests.

5. The wearing article according to claim 1, wherein said second panel comprises a porous liquid-pervious thermoplastic synthetic resin sheet.

* * * * *

UNITED STATES PATENT AND TRADEMARK OFFICE
CERTIFICATE OF CORRECTION

| | | |
|---|---|---|
| PATENT NO. | : 7,015,370 B2 | Page 1 of 1 |
| APPLICATION NO. | : 10/634081 | |
| DATED | : March 21, 2006 | |
| INVENTOR(S) | : Maki Watanabe, Miou Suzuki and Masashi Nakashita | |

It is certified that error appears in the above-identified patent and that said Letters Patent is hereby corrected as shown below:

<u>Column 8,</u>
Line 30, should be -- of water-absorbent fibers, 0 to 80 wt % of super-absorbent --.
Line 46, should be -- each of said plurality of narrow strips being formed on an --.

Signed and Sealed this

Fourth Day of July, 2006

JON W. DUDAS
*Director of the United States Patent and Trademark Office*